United States Patent [19]

Heimreid

[11] Patent Number: 4,758,236
[45] Date of Patent: Jul. 19, 1988

[54] ARRANGEMENT IN AN INFUSION KIT

[76] Inventor: Bent Heimreid, Hagerup Knutssons vei 22, N-3940 Heistad, Norway

[21] Appl. No.: 947,395

[22] Filed: Dec. 29, 1986

[30] Foreign Application Priority Data

May 12, 1986 [NO] Norway ................. 861886

[51] Int. Cl.⁴ ............................................. A61M 5/16
[52] U.S. Cl. ...................... 604/251; 604/85
[58] Field of Search ............... 604/56, 82–85, 604/246, 251–255

[56] References Cited

U.S. PATENT DOCUMENTS 3,001,525  9/1961  Hendricks ............... 604/251 X
3,311,268  3/1967  Fields ................... 604/251 X

FOREIGN PATENT DOCUMENTS 1258222  3/1961  France ................... 604/251

Primary Examiner—Dalton L. Truluck
Attorney, Agent, or Firm—Cushman, Darby & Cushman

[57] ABSTRACT

An arrangement in an infusion kit comprising an infusion container with a connected air trap/drop counter for drops, with a discharge piece provided in said trap/counter, and wherein the top of said trap/counter is shaped as a hollow cone or the like, tapering upwards in a working position, said discharge piece extending downwards from the apex of said cone. Said arrangement, furthermore, comprises a drainage hole provided in said discharge piece at its base in the top of said air trap/drop counter.

1 Claim, 1 Drawing Sheet

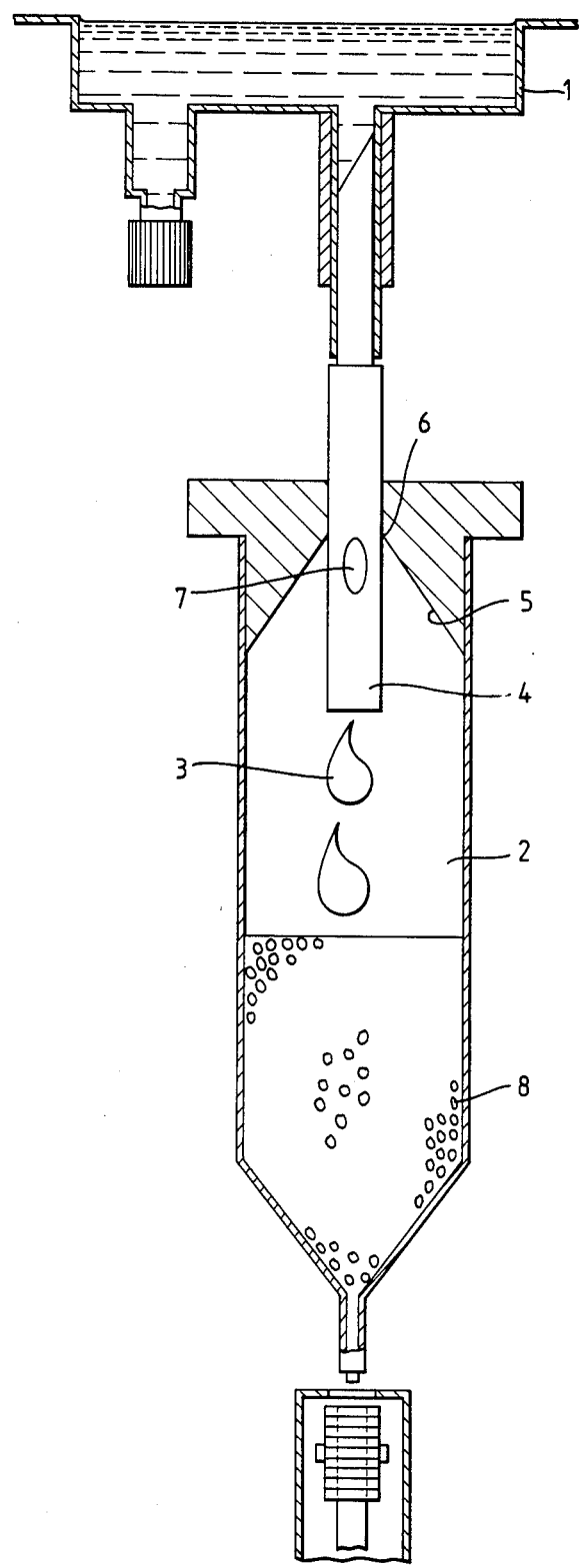

ARRANGEMENT IN AN INFUSION KIT

The present invention relates to an arrangement in infusion kits comprising an infusion container with a connected air trap/drop counter.

The known infusion kit used in health services to day essentially consists of a container for infusion liquid, previously mainly produced in the shape of a bottle, but lately to an increasing extent produced from plastic in the shape of a bag, and with an air trap/drop counter which is connected with said container and which, via necessary connections, cut-off means, and the like, finally opens into a cannula intended as an inlet channel to the patient.

Said air trap/drop counter was commonly provided with an discharge piece which would simplify counting in cases where this was of essential importance.

In certain cases, however, it may be desirable to mix the infusion liquid with a volume, adapted to the volume of infusion liquid, of an additive in liquid or solid state.

Such treatment, however, was bothersome and time consuming with the infusion kits known so far.

The most common infusion kit to day, as indicated above, comprises a suitable container connected with an air trap/drop counter. From what is the top of the drop counter in a working position a discharge piece projects and simplifies the counting of drops for adjustment of the infusion velocity.

Furthermore, modern infusion kits are designed with a drop counter/air trap made of plastic.

Due to this fact, the desired additive can be dosed in the drop counter, permitting a closed mixing system to be achieved, where said additive is mixed with infusion liquid from the bag of drop counter in said drop counter.

In order to ensure a homogenous mixture, as indicated above, it will be necessary in this case to pump the liquid back into the infusion bag by the aid of a soft drop counter. In the infusion kits known to day this is, however, impossible, as there will always remain liquid in said drop counter because of said discharge piece, which makes the amount of liquid dependent on the length of said discharge piece.

It is an object of the present invention to eliminate the drawback of known infusion kits, and the invention, thus, relates to an arrangement of an infusion kit of the kind mentioned above, where the top of said air trap/drop counter is shaped as a hollow cone or the like, tapering upwards in a working position, with said discharge piece depending from the apex of said cone, and the invention is characterized by the fact that said discharge piece is provided with a drainage hole at its base in the top of droo counter/air trap chamber.

The invention is now disclosed in more detail with reference to the enclosed drawing.

An infusion container 1 is filled with infusion liquid which it is desirable to mix with an additive 8 that was poured into a drop counter/air trap on production.

If said additive is present in a liquid state the drop-counter of the combination is turned upside-down, and by the aid of the soft walls of the counter the additive is pumped into the bag where mixing can take place.

If, however, said additive is present in a solid state the kit is held in a working position and liquid is then pumped down into said counter in a sufficient volume to dissolve the solid substance placed there.

By turning the kit upside-down it is then possible to pump the solution back into said bag where it is easily mixed with the remaining infusion liquid. By the aid of the arrangement according to the invention it is ensured that no liquid will remain in said drop counter.

If the volume of infusion liquid pumped down from said infusion bag should be insufficient to dissolve the additive placed there in advance, the procedure may in a very simple and rapid manner be repeated, until all additive is rinsed out of the drop counter/air trap and into said infusion bag. Then the desired infusion may be carried out in a conventional manner.

By the aid of the arrangement according to the invention it is ensured that there is no hazard of any desired additive remaining in the chamber which in a working position is placed above the discharge end of discharge piece and that all additive is used in the intended manner.

Furthermore, it is very easy and simple to provide a mixture as disclosed and at the same time a system is provided which ensures the best possible hygiene and safety.

Having described my invention, I claim:

1. An infusion set comprising: a container for holding a liquid infusion; an air/drop counter having an interior space which is in communication with an outlet opening at one end of said counter space, the opposite end of said counter space being defined by a generally conically shaped wall which converges to an apex in a direction away from said one end of said counter space; and a tubular discharge piece connecting the interior of said container with said counter space, said discharge piece having an end extending through said apex and into said counter space, said end of said piece having a laterally-facing drainage hole at a location within the space defined by said conically shaped wall.

* * * * *